(12) United States Patent
Ghanavi et al.

(10) Patent No.: US 9,617,562 B2
(45) Date of Patent: Apr. 11, 2017

(54) NONVIRAL TARGETED NANOPARTICLE SYSTEM FOR GENE TRANSFER AND DRUG DELIVERY

(71) Applicants: Jalaledin Ghanavi, Tehran (IR); Poopak Farnia, Tehran (IR)

(72) Inventors: Jalaledin Ghanavi, Tehran (IR); Poopak Farnia, Tehran (IR)

( * ) Notice: Subject to any disclaimer, the term of this patent is extended or adjusted under 35 U.S.C. 154(b) by 0 days.

(21) Appl. No.: 14/475,708

(22) Filed: Sep. 3, 2014

(65) Prior Publication Data
US 2014/0370500 A1  Dec. 18, 2014

(51) Int. Cl.
| | | |
|---|---|---|
| *C12N 15/88* | (2006.01) | |
| *A61K 47/24* | (2006.01) | |
| *A61K 47/26* | (2006.01) | |
| *A61K 47/42* | (2006.01) | |
| *A61K 9/51* | (2006.01) | |

(52) U.S. Cl.
CPC ............ *C12N 15/88* (2013.01); *A61K 9/5123* (2013.01); *A61K 9/5161* (2013.01); *A61K 9/5169* (2013.01); *C12N 2810/00* (2013.01); *Y10T 428/2982* (2015.01)

(58) Field of Classification Search
None
See application file for complete search history.

(56) References Cited

PUBLICATIONS

Zhang, et al. (Jul. 2006) "Dynamical Heterogeneity in Supported Lipid Bilayers", MRS Bulletin, 31: 527-31.*
http://www.dictionary.com/browse/gene, author unknown, published by Houghton Mifflin Co., From the American Heritage New Dictionary of Cultural Literacy, 3rd Ed., printed on Jan. 2, 2017, 1 page.*

* cited by examiner

*Primary Examiner* — Robert M Kelly
(74) *Attorney, Agent, or Firm* — Barry Choobin; Patent 360

(57) ABSTRACT

The embodiments herein provide a nanoparticle system for targeted gene delivery or a drug delivery and a method of synthesizing the same. The nanoparticle composition for targeted gene transfer and drug delivery comprises a protein, a chitosan and a lipid. A method of synthesizing the nanoparticles involves preparing a gelatine and chitosan gel. A milky colloid solution is prepared with the gelatine, chitosan solution and a phosphatidylcholine. The milky colloid is homogenized for the self assembly of the nanoparticles. The milky colloid is subjected to high speed and high pressure homogenizer. The CHO cells are transfected with nanoparticles and lipofectamine 2000 for comparing the transfection efficiency. The nanoparticles deliver DNA, RNA, ribozyme and nucleotide sequences. The nanoparticles deliver lipophylic and hydrophilic drugs. The transfection efficiency of gene and drug is higher when the target cells are transferred with nanoparticles, compared to the cells transferred with lipofectamine 2000.

10 Claims, 12 Drawing Sheets

NONVIRAL TARGETED NANOPARTICLE SYSTEM FOR GENE TRANSFER AND DRUG DELIVERY

BACKGROUND

Technical Field

The embodiments herein generally relate to the field of molecular nanotechnology. The embodiments herein particularly relate to nanomedicines based drug delivery systems and gene transfer systems. The embodiments herein more particularly relate to a method and system for synthesizing nanoparticles for drug delivery and gene transfer.

Description of the Related Art

In nanotechnology, a particle is defined as a small object that becomes a whole unit with respect to its transport and properties. The particles are further classified according to the diameter. The "nanoparticles" have a diameter within a range of 1 and 100 nanometer.

Nanotechnology has offered many advantages for novel drug delivery systems and gene delivery systems in terms of both time-controlled drug delivery, site-directed drug delivery and site-directed gene delivery. These advantages are mainly derived from the very small (submicron) sizes of the nanostructures used as nanocarriers for drugs or genes as well as the possibility of engineering the carrier structure and/or surface according to the particular biological requirements.

"Nanomedicine" is the medical application of nanotechnology. Nanomedicine ranges from the medical applications of nonmaterial's to nano-electronic biosensor and even possible future applications of molecular nanotechnology.

The current problems for nano-medicine involve understanding the issues related to toxicity and the environmental impact on a nanoscale material. The nano-medicine has provided the possibility of delivering drugs and genes to specific cells using nanoparticles. The overall drug consumption and side effects are lowered significantly by depositing an active agent only in a morbid region at a required and appropriate dosage thereby eliminating a need for a higher dosage.

The drug delivery and gene delivery systems such as lipid or polymer based nanoparticles are designed to improve the pharmacological and therapeutic properties. Further, the metal based nanoparticles are also designed and developed to deliver the drugs and genes. The drug delivery system or gene delivery system consists of nanoparticles, nanoemulsions, liposomes and micelles. The polymeric and lipid based nano systems improved drug bioavailability and protect the encapsulated drug or gene from enzymatic attack.

The nanoparticles have been successfully applied as a drug delivery system and as a gene delivery system. The commonly used metals for nano-drug delivery system and gene delivery system include but not limited to gold, silver, platinum etc. The nanoparticles have been successfully applied as a delivery system for plasmid DNA in gene therapy. The nanoparticles provide an opportunity for targeting the DNA of interest into specific tissues or cells by attaching specific ligands on the surface of the nanoparticles.

The metal based nanoparticles for the drug delivery system show toxicity. The recent studies in this arena have shown that positively charged gold nanoparticles are found to enter kidney, while negatively charged gold nanoparticles remained in the liver and spleen. The positive surface charges of the nanoparticles decreases the rate of opsonization of nanoparticles in the liver, thereby affecting the excretory pathway. Even a relatively small size of the nanoparticles such as 5 nm can become compartmentalized in the perinephral tissues, and accumulate in the body over tissues. The advancement of research proves that targeting and distribution can be augmented by nanoparticles and the dangers of nano-toxicity have become an important question for the medical use in drug delivery.

Apart from the metal nanoparticles for gene delivery, there are two main systems for gene delivery. The two systems are viral vectors and non viral vectors.

Viral vectors are commonly used tool by molecular biologists to deliver genetic material into cells. The process can be performed inside a living organism (in vivo) or cell culture (in vitro). The viruses have evolved specialized molecular mechanisms to efficiently transport their genomes inside the cells they infect. The delivery of genes by viruses is termed as transduction. The viral vectors show high transfection efficiency, but there are some limitations of viral vectors such as non specificity, immunogenicity to the target cells and oncogenic effects. Also the viral vectors to deliver genetic material to cells come with logistical problems. There are limited member of viral vectors available can cause the body to develop an immune response, if the vector is seen as a foreign invader by the immune system. The viral vectors can infect healthy cells. It has been observed that the viral vectors get mutated and become virulent in nature.

The non viral vectors for gene therapy are preferred over viral vectors. The two main types of non viral gene delivery vectors are cationic liposomes and cationic polymers. The cationic polymers have been used to deliver DNA both in vitro and in vivo in terms of biocompatibility and low cytotoxicity. Specifically the cationic liposomes have potential to act as a delivery vector. However, their applications are limited to local delivery due to low stability and rapid degradation in the body. The cationic polymers include but not limited to chitosan, collagen, gelatin etc.

Chitosan is a natural cationic polymer obtained by deacetylation of its parent polymer chitin. Chitin is a polysaccharide widely distributed in nature. Chitosan has good biocompatibility, biodegradability, atoxicity and is non-allergic in nature. Chitosan is polycationic polymer and a weak base with a pKa value of 6.5. The physiochemical, structural, thermal, mechanical, biological and rheological properties of this polymer vary significantly with its molecular weight and degree of acetylation. Chitosan has been widely employed in gene delivery. Chitosan delivers drug or gene into the target cell by interacting with the cell membrane. The interaction of protonated amine group in chitosan with cell membrane results in a reversible structural reorganization of protein associated with tight junctions. The interaction leads to opening of tight junctions and thereby facilitating drug or gene delivery. Chitosan as a gene vector has disadvantages like relative inefficiency and low specificity. Also chitosan exhibit problems such as low solubility and low transfection efficiency.

Collagen is an abundant structural protein in all animals. In humans collagen comprises one third of the total protein. Collagen accounts for three quarters of the dry weight of skin and it is the main component of the extracellular matrix (ECM). Collagen is an important biomaterial in medical applications due to its special characteristics such as biodegradability and weak antigenicity. Thus collagen is a new type of biomaterial, which has been used in drug delivery systems and tissue engineering. A sequence motif of Arginine-Glycine-Aspargine (RGD) acts as cell-adhesion recognition motif. This sequence motif is found in collagen, fibronectin and tenascin C. The RGD sequence is the ligand for integrin-mediated cell adhesion, which involves a cascade of four overlapped reactions i.e. cell attachment, cell spreading, focal adhesion and cell cycle. The RGD sequence is the most effective cell recognition motif and has been used to stimulate cell adhesion on artificial surfaces. The soluble RGD peptide can inhibit the cell adhesion because it is the antagonist as well as the recognition sequence for integrin. The defining feature of collagen is an elegant structural motif in which three parallel polypeptide strands in a left handed, polyproline type-II (PPII) helical conformation coil about each other with a one-residue stagger to form a right handed triple helix. The tight packing of PPII helices within the triple helix mandates that every third residue is glycine (Gly). This results in a repeating sequence of XaaYaaGly. Xaa and Yaa can be any amino acid. This repeat occurs in all types of collagen, although it is disrupted at certain locations within the triple-helical domain of non-fibrillar collagens. There is a clear bias for Glutamine, Leucine and Phenylalanine in X position whereas Arginine and Lysine are seen to be preferred in the Y position of the Gly-X-Y triplets in all the five collagen chains. Interestingly Glycine and Threonine also show a preference for Y position in Type I and Type II collagens wile Methionine shows a similar preference in Type I, II and IV collagens. The residues showing preference for Y position can help stabilize triple helices as well as assemblies of triple helices through additional interactions.

Liposomes or phospholipid vesicles are self assembled colloidal particles that occur naturally and can be prepared artificially. Liposomes were introduced as drug delivery vehicles in 1970. The liposomes are mainly used for antifungal and anticancer drug delivery agents. The liposomes or phospholipids are polar lipids, whereas triglycerides are neutral lipids. The phospholipids are amphipathic molecules due to the presence of both polar head and non-polar tail. The phospholipids have the glycerol backbone structure as the neutral glycerides, but differ in the ester linkages resulted from a phosphoryl ester. In other words the phospholipids are composed of glycerol, 2 fatty acids and a phosphoryl ester group bonded to the third alcohol carbon of the glycerol backbone. The phospholipids are the primary building bocks of all cellular membranes. The vital organs such as the liver, reproductive tract and muscles contain high concentration of phospholipids. The membrane functions include cellular transport of nutrients and wastes, internal cellular pressure regulation and ion exchange.

Chitosan and glycerol phosphate (GP) system have shown potential for drug delivery and cell encapsulation. Gelation form of chitosan in glycerol phosphate is obtained when GP is added to chitosan solution. The pH of the solution increases as a result of the neutralizing phosphate groups. The chitosan-GP solutions can maintain their liquid state at physiological pH. The forces involved in the gelation process are hydrogen bonding, hydrophobic and electrostatic interactions. Chitosan is used for the production of nanoparticles by ionotropic gelation with tripolyphosphate.

The design of nanoparticle used for carrier of drugs and genes for treatment of diseases are desired to be delivered to a target cell and could be overcome of pharmaceutical and biopharmaceutical barriers and attached to target cell. The cationic liposomes have potential as a gene delivery vector; however their applications are limited to local delivery due to low stability and rapid degradation in the body. The chitosan is a cationic polymer has been used to deliver DNA both in vitro and in vivo with low cytotoxicity but still has some problem such as relative inefficiency and low specificity.

The combination of chitosan, collagen and phospholipids approve affinity to gene or drug, targeting and controlled release and protection from destroying of gene or drug until effect.

Hence there is a need to develop a nanoparticle based drug delivery system and gene delivery system without any threat of cytotoxicity. Also there is a need for a nanoparticle drug delivery system and gene delivery system for site directed gene delivery to release the drug slowly in a controlled manner to an action site. Further there is a need to develop a method for synthesizing the organic biomolecule based nanoparticle drug delivery system and gene delivery system.

The above mentioned shortcomings, disadvantages and problems are addressed herein and which will be understood by reading and studying the following specification.

OBJECTIVES OF THE EMBODIMENTS

The primary objective of the embodiments herein is to synthesize a novel and improved non-viral nanoparticle composition for targeted gene transfer and drug delivery.

Another objective of the embodiments herein is to synthesize the non-viral nanoparticle composition for targeted gene transfer and drug delivery comprising a complex of cell targeting ligand consisting of protein, chitosan and lipid or a derivative thereof.

Yet another objective of the embodiments herein is to synthesize the non-viral nanoparticle composition comprising the proteins consisting of cationic or anionic collagen or gelatin or a derivative thereof.

Yet another objective of the embodiments herein is to synthesize the non-viral nanoparticle composition comprising RGD (Arg-Gly-Asp) sequence as a cell adhesion recognition motif in collagen or gelatin or a derivative thereof.

Yet another objective of the embodiments herein is to synthesize the non-viral nanoparticle composition comprising the lipids consisting of phospholipid or sterol or glycerol or monoglyceride or glyceride or triglyceride or fat-soluble vitamin or saturated or unsaturated free fatty acid glycolipid or a derivative thereof or a combination thereof.

Yet another objective of the embodiment herein is to synthesize the non-viral nanoparticle composition comprising lipids, so that the hydrophobic lipid tails and heterogeneous dynamics in the nanoparticle affect the cell membrane flexibility for the attachment and nanoparticle release into the cell.

Yet another objective of the embodiment herein is to synthesize the non-viral nanoparticle formation as a result of self assembly and/or high-speed stirring and/or high pressure condition or high pressure method, ethanol or ether injection method or ultrasonication method.

Yet another objective of the embodiment herein is to synthesize the non-viral nanoparticle composition in which the nanoparticles have a mean particle size between 50 and 400 nanometers.

Yet another objective of the embodiment herein is to synthesize the non-viral nanoparticle composition to deliver genes selected from a group consisting of plasmid DNA, single- or double stranded RNA, siRNA, RNA vaccine, an antisense and a ribozyme.

Yet another objective of the embodiment herein is to synthesize the non-viral nanoparticle composition to deliver drugs selected from a group consisting of lipophilic drugs and hydrophilic drugs.

Yet another objective of the embodiment herein is to synthesize the non-toxic non-viral nanoparticle composition to deliver drugs or genes, so that the nanoparticle adheres to the mucosal surface and openings of tight junctions between epithelial cells for the intravenous drug delivery to brain via blood brain barrier.

Yet another objective of the embodiment herein is to synthesize the non-viral nanoparticle composition to deliver drugs or genes in acidic pH conditions.

These and other objects and advantages of the embodiments herein will become readily apparent from the following detailed description taken in conjunction with the accompanying drawings.

SUMMARY

The various embodiments herein provide a system and a method for the synthesis of the nanoparticle based drug delivery and gene delivery system. The drug or gene delivery nanoparticles are prepared by a combination of chitosan, collagen and phospholipid. The combination of chitosan, collagen and phospholipid provide affinity to gene or drug, controlled release and protection of gene or drug from deterioration until delivery to the target site.

According to one embodiment herein, a nanoparticle composition for targeted gene transfer and drug delivery to cell comprises a complex of a ligand, and wherein the ligand is cell targeting ligand. The ligand comprises a protein, a chitosan, and a lipid or a derivative thereof. The chitosan has a positive charge component, and the lipid has a negative charge. The protein, the chitosan and the lipid have an electrostatic attraction.

According to one embodiment herein, the protein is selected from a group consisting of a collagen, a gelatin, an elastin, a derivative of the elastin, tripeptide motif system having Xaa position, a hormone, a cytokine, an antibody, an affibody, or a combination thereof. The collagen is a collagen of type I or type II or type III or type IV or type V or type VI or type VII or type VIII. The hormone is a thyroid hormone or a polypeptide harmone. The tripeptide motif system is RGD (Arg-Gly-Asp) tripeptide motif system, and the RGD (Arg-Gly-Asp) tripeptide motif system recognizes the target cell. The protein performs cell adhesion or cell signaling or both, also the proteins or polypeptide increases or reduces a cell function. The protein has a concentration of 0.005 mmol to 1 mmol, preferably in a range of 0.05 to 0.5 mmol, and more preferably in a range of 0.01 to 0.1 mmol.

According to one embodiment herein, the lipid is selected from a group consisting of a phospholipid, a sterols, a steroid, a glycerol, a monoglyceride, a diglyceride, a triglyceride, a fat soluble vitamin, a saturated fatty acid, an unsaturated fatty acid, a glycolipid or a combination thereof or a derivative thereof. The phospholipid is neutral or anionic. The phospholipid has the hydrophobic lipid tails, and the hydrophobic lipid tails activates heterogenous dynamic action in the nanoparticle to causes cell membrane to become flexible for attaching the nanoparticle and releasing the nanoparticle in a target cell. The concentration of the lipid is within a range of 0.01 mmol to 200 mmol, preferably in a range of 0.1 to 50 mmol and more preferably in a range of 1 to 2 mmol.

According to one embodiment herein, the phospholipid is selected from a group consisting of a phosphatidyl choline, a phosphatidyl glycerol, a phosphatidylethanolamine, a phisphatidic acid, a phosphatidyl serine, a sphingomyelin, a phoshatidyl inositol, a cardiolipin and a lecithin. The phosphatidyl choline is selected from a group consisting of a distearoylphosphatidyl choline, a diinoleoylphosphatidyl choline, a dioleoylphosphatidyl choline, a myristoylpalmitoylphosphatidyl choline, a myristoylstearoylphosphatidyl choline, a dilauroylphosphatidyl choline, a dimyrostoylphosphatidyl choline, a dipalmitoylphosphatidyl choline and a palmitoylstearoylphosphatidyl choline. The phosphatidyl glycerol is selected from a group consisting of a dilauroylphosphatidyl glycerol, a dimyristoylphosphatidyl glycerol, a dipalmitoylphosphatidyl glycerol, a distearoylphosphatidyl glycerol, a dioleoylphosphatidyl glycerol, a dilinoleoylphosphatidyl glycerol, a myristoylpalmitoyl, a phosphatidyl glycerol, a myristoylstearoylphosphatidyl glycerol and a palmotoylstearoylphosphatidyl glycerol. The phaosphatidyl ethanolamine is selected from a group consisting of a dipalmitoylphosphatidyl ethanolamine, a dimyristoylphosphatidyl ethanolamine, a myristolpalmitoylphosphatidyl ethanolamine, a distearoylphosphatidyl ethanolamine, a dioleoylphosphatidyl ethanolamine, a dilauroylphosphatidyl ethanolamine, a dilinoleoylphosphatidyl ethanolamine, a myristoylsteroylphosphatidyl ethanolamine and a palmitoylstearoylphosphatidyl ethanolamine. The phospholipid induces an electrostatic attraction between the charged groups of the nanoparticles to regulate a gene or a drug delivery, to regulate a solubility of a lipid component of nanoparticles and to transfect the nanoparticles to the target cell.

According to one embodiment herein, the steroid is selected from a group consisting of a corticosteroid, sex steroid, cholesterol, bile acid, sterol and a derivative thereof. The steroid modulates the fluidity of the nanoparticle and regulation of the target cell function. The corticosteroid is selected from a group consisting of a glucocorticoid and a mineralocorticoid. The sex steroid is selected from a group consisting of an androgen, an estrogen, and a progesterone.

According to one embodiment herein, the glycolipid is selected from a group consisting of a glycerol glycolipid, a glycosphingolipid, a stearyl glyceside and a ganglioside esterified stearyl glycoside, and wherein the glycerol glycolipids is selected from a group consisting of a diglycosyldi glyceride, a digalactosyldi glyceride, a galactosyldi glyceride and a glycosyldiglyceride. The glycosphingolipid is selected from a group consisting of a galactocerebroside, a stearylglucoside, and a ganglioside esterified stearylglycoside. The glycolipid causes stability of nanopariticles and attachment to target cell membrane.

According to one embodiment herein, the unsaturated fatty acid is selected from a group consisting of a myristoleic acid, a palmitoleic acid, a sapienic acid, an oleic acid, an elaidic acid, a vaccenic acid, a linolic acid, a linoelaidic acid, α-linolenic acid, an arachidonic acid, an eicosapentaenoic acid, an erucic acid and a docosahexanoic acid.

According to one embodiment herein, the saturated fatty acid is selected from a group consisting of a caprylic acid, a capric acid, a lauric acid, a myristic acid, a palmitic acid, a stearic acid, an arachidic acid, a behenic acid, a lignoceric acid and a cerotic acid.

According to one embodiment therein, the lipid in the nanoparticle is a single type or a mixture of two types or a mixture of two or more lipid types, and wherein the lipid component in the nanoparticle composition is a combination of phospholipid and steroid or preferably a glycolipid or a combination of a phosphatidyl choline and a steroid or more preferably the glycolipid.

According to one embodiment herein, the concentration of hormone or hormone like polypeptide or a thyroid hormone or cytokine or an antibody or an affibody or a combination thereof is in a physiological range of the target cell.

According to one embodiment herein, the nanoparticle has a mean particle size of 50 to 400 nanometer.

According to one embodiment herein, the nanoparticle delivers a gene or a drug, and the gene is selected from a group consisting of a plasmid DNA, a single stranded RNA, a double stranded RNA, a siRNA, a RNA vaccine, an antisense strand of nucleotide and a ribozyme. The drug is selected from a group consisting of a lipophylic drug and a hydrophilic drug.

According to one embodiment herein, a method of synthesizing targeted gene transfer and drug delivery nanoparticle, comprises the steps of preparing a gelatin and chitosan gel. Further a milky colloid solution with the gelatin and chitosan is added with a phosphatidylcholine. The milky colloid solution is subjected to homogenizing in a high speed homogenizer and a high pressure homogenizer for a self assembly of nanoparticles. The last step is transfecting a Chinese Hamster Ovary cells (CHO cells) with the nanoparticles and a lipofectamine 2000 for comparing a transfection efficiency.

According to one embodiment herein, the steps of preparing a gelatin and chitosan gel comprises dissolving 1.76 gram of chitosan in 100 ml of 0.8% of acetic acid and incubating the chitosan solution in a shaker incubator for 16 hours at 37° C. with 120 rpm. The next step is dissolving a 0.4 to 0.6 gram of gelatin in 100 ml of phosphate buffer and incubating the gelatin solution in a shaker incubator for 3 hours at 40° C. with 120 rpm. The 10 ml of dissolved gelatin solution is mixed with the 70 ml of chitosan solution to obtain a solution mixture. The solution mixture is rotated in an incubator shaker for 30 minutes at 37° C. with 140 rpm and obtaining the gelatin chitosan gel.

According to one embodiment herein, the steps of preparing a milky colloid solution comprises dissolving 1.76 gram of chitosan in 100 ml of a 0.8% acetic acid. Further 0.4 to 0.6 gram of gelatin is dissolved in 100 ml of phosphate buffer. The next step is mixing 10 ml of dissolved gelatin with 70 ml of chitosan to obtain a solution mixture. The gelatin and chitosan solution mixture are mixed with a phosphatidyl choline solution. The phosphatidylcholine solution is prepared by dissolving the 0.2 gram of phosphatidylcholine in 10 ml chloroform. After mixing the gelatin and chitosan solution mixture, the milky colloid solution is obtained.

According to one embodiment herein, the step of homogenizing the milky colloid solution for self assembly comprises the steps of pouring a 15 ml of gelatin-chitosan gel into a flask. The gel is stirred on a high speed magnetic stirrer. A 5 ml (200 μl/minute) of milky colloid solution is added to the gel to get a mixture. The mixture is homogenized to obtaining the nanoparticles with a size in the range of 400 nm to 700 nm.

According to one embodiment herein, the step of homogenizing milky colloid solution with a high speed homogenizer comprises the steps of mixing 15 ml of gelatin and chitosan gel with 5 ml of milky colloid in a 50 ml falcon tube to get a mixture. The mixture is subjected to a high speed homogenizer, and obtaining the nanoparticles with a size in the range of 50-400 nm.

According to one embodiment herein, the steps of homogenizing milky colloid solution with a high pressure device comprises mixing 15 ml of gelatin-chitosan gel with 5 ml of milky colloid. The tube is subjected to a high pressure homogenizer, and the nanoparticles with a size in the range of 100-400 nm are obtained.

According to one embodiment herein, the steps of transfecting a Chinese Hamster Ovary cells (CHO) cells, with the nanoparticles comprises culturing the CHO cells at a concentration of $4 \times 10^4$ cells per well into 24 well culture plates containing opti-MEM (1×). 1 μl of pEGFP-N1 plasmid and 2 μl of nanoparticles are diluted separately in a 50 μl of opti-MEM media. The diluted plasmids are incubated at a room temperature for 5 minutes. Equal volumes of the diluted plasmid (50 μl) and the nanoparticles (50 μl) are mixed and incubated at a room temperature for 30 minutes. 100 μl of diluted plasmid and nanoparticles are added into each well of the 24 well culture plate containing CHO cells. The light emitting fluorescent cells are detected 24 hours after transfecting the cells with the nanoparticles. The plasmid transfected cells by the nanoparticles emit a green fluorescent light, and 85% CHO cells are transfected with the nanoparticles facilitated transfection. The concentration of a recombinant protein (sFLT1) is 597 mg/L per cell culture supernatant after the cells are transfected with the plasmid.

According to one embodiment herein, the method of transfecting a Chinese Hamster Ovary (CHO) cells with the lipofectamine 2000 comprises culturing the CHO cells at a concentration of $4 \times 10^4$ cells per well into 24 well culture plates containing opti-MEM (1×). 1 μl of pEGFP-N1 plasmid 2 μl of the lipofectamine 2000 are diluted separately in a 50 μl of opti-MEM media. The diluted plasmids are incubated at a room temperature for 5 minutes. Equal volumes of the diluted plasmid (50 μl) and the lipofectamine 2000 (50 μl) are mixed and incubated at a room temperature for 30 minutes. 100 μl of diluted plasmid and lipofectamine 2000 are added into each well of the 24 well culture plate containing CHO cells. The light emitting fluorescent cells are detected 24 hours after transfecting the cells with the nanoparticles. The plasmid transfected cells by nanoparticles emit a fluorescent light. The rate of cell trasfection is 60-70% when lipofectamine 2000 is used. The concentration of recombinant protein (sFLT1) is 103 mg/L per cell culture supernatant after the cells after the cells are transfected with the lipofectamine 2000.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
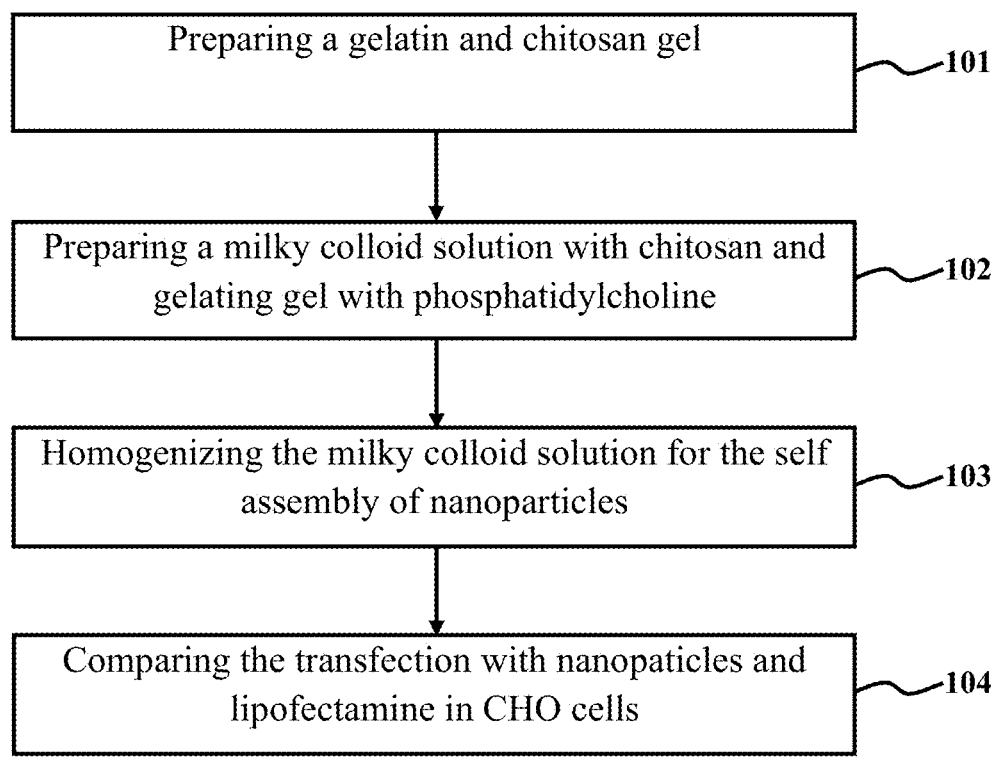
FIG. 1 is a flowchart illustrating the process of synthesizing non-viral drug and gene delivery nanoparticle, according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a system and a method for the synthesis of the nanoparticle based drug delivery and gene delivery system. The drug or gene delivery nanoparticles are prepared by a combination of chitosan, collagen and phospholipid. The combination of chitosan, collagen and phospholipid provide affinity to gene or drug, controlled release and protection of gene or drug from deterioration until delivery to the target site.

According to one embodiment herein, a nanoparticle composition for targeted gene transfer and drug delivery to cell comprises a complex of a ligand, and wherein the ligand is cell targeting ligand. The ligand comprises a protein, a chitosan, and a lipid or a derivative thereof. The chitosan has a positive charge component, and the lipid has a negative charge. The protein, the chitosan and the lipid have an electrostatic attraction.

According to one embodiment herein, the protein is selected from a group consisting of a collagen, a gelatin, an elastin, a derivative of the elastin, tripeptide motif system having Xaa position, a hormone, a cytokine, an antibody, an affibody, or a combination thereof. The collagen is a collagen of type I or type II or type III or type IV or type V or type VI or type VII or type VIII. The hormone is a thyroid hormone or a polypeptide harmone. The tripeptide motif system is RGD (Arg-Gly-Asp) tripeptide motif system, and the RGD (Arg-Gly-Asp) tripeptide motif system recognizes the target cell. The protein performs cell adhesion or cell signaling or both, also the proteins or polypeptide increases or reduces a cell function. The protein has a concentration of 0.005 mmol to 1 mmol, preferably in a range of 0.05 to 0.5 mmol, and more preferably in a range of 0.01 to 0.1 mmol.

According to one embodiment herein, the lipid is selected from a group consisting of a phospholipid, a sterols, a steroid, a glycerol, a monoglyceride, a diglyceride, a triglyceride, a fat soluble vitamin, a saturated fatty acid, an unsaturated fatty acid, a glycolipid or a combination thereof or a derivative thereof. The phospholipid is neutral or anionic. The phospholipid has the hydrophobic lipid tails, and the hydrophobic lipid tails activates heterogenous dynamic action in the nanoparticle to causes cell membrane to become flexible for attaching the nanoparticle and releasing the nanoparticle in a target cell. The concentration of the lipid is within a range of 0.01 mmol to 200 mmol, preferably in a range of 0.1 to 50 mmol and more preferably in a range of 1 to 2 mmol.

According to one embodiment herein, the phospholipid is selected from a group consisting of a phosphatidyl choline, a phosphatidyl glycerol, a phosphatidylethanolamine, a phisphatidic acid, a phosphatidyl serine, a sphingomyelin, a phoshatidyl inositol, a cardiolipin and a lecithin. The phosphatidyl choline is selected from a group consisting of a distearoylphosphatidyl choline, a diinoleoylphosphatidyl choline, a dioleoylphosphatidyl choline, a myristoylpalmitoylphosphatidyl choline, a myristoylstearoylphosphatidyl choline, a dilauroylphosphatidyl choline, a dimyrostoylphosphatidyl choline, a dipalmitoylphosphatidyl choline and a palmitoylstearoylphosphatidyl choline. The phosphatidyl glycerol is selected from a group consisting of a dilauroylphosphatidyl glycerol, a dimyristoylphosphatidyl glycerol, a dipalmitoylphosphatidyl glycerol, a distearoylphosphatidyl glycerol, a dioleoylphosphatidyl glycerol, a dilinoleoylphosphatidyl glycerol, a myristoylpalmitoyl, a phosphatidyl glycerol, a myristoylstearoylphosphatidyl glycerol and a palmotoylstearoylphosphatidyl glycerol. The phaosphatidyl ethanolamine is selected from a group consisting of a dipalmitoylphosphatidyl ethanolamine, a dimyristoylphosphatidyl ethanolamine, a myristolpalmitoylphosphatidyl ethanolamine, a distearoylphosphatidyl ethanolamine, a dioleoylphosphatidyl ethanolamine, a dilauroylphosphatidyl ethanolamine, a dilinoleoylphosphatidyl ethanolamine, a myristoylsteroylphosphatidyl ethanolamine and a palmitoylstearoylphosphatidyl ethanolamine. The phospholipid induces an electrostatic attraction between the charged groups of the nanoparticles to regulate a gene or a drug delivery, to regulate a solubility of a lipid component of nanoparticles and to transfect the nanoparticles to the target cell.

According to one embodiment herein, the steroid is selected from a group consisting of a corticosteroid, sex steroid, cholesterol, bile acid, sterol and a derivative thereof. The steroid modulates the fluidity of the nanoparticle and regulation of the target cell function. The corticosteroid is selected from a group consisting of a glucocorticoid and a mineralocorticoid. The sex steroid is selected from a group consisting of an androgen, an estrogen, and a progesterone.

According to one embodiment herein, the glycolipid is selected from a group consisting of a glycerol glycolipid, a glycosphingolipid, a stearyl glyceside and a ganglioside esterified stearyl glycoside, and wherein the glycerol glycolipids is selected from a group consisting of a diglycosyldi glyceride, a digalactosyldi glyceride, a galactosyldi glyceride and a glycosyldiglyceride. The glycosphingolipid is selected from a group consisting of a galactocerebroside, a stearylglucoside, and a ganglioside esterified stearylglycoside. The glycolipid causes stability of nanopariticles and attachment to target cell membrane.

According to one embodiment herein, the unsaturated fatty acid is selected from a group consisting of a myristoleic acid, a palmitoleic acid, a sapienic acid, an oleic acid, an elaidic acid, a vaccenic acid, a linolic acid, a linoelaidic acid, α-linolenic acid, an arachidonic acid, an eicosapentaenoic acid, an erucic acid and a docosahexanoic acid.

According to one embodiment herein, the saturated fatty acid is selected from a group consisting of a caprylic acid, a capric acid, a lauric acid, a myristic acid, a palmitic acid, a stearic acid, an arachidic acid, a behenic acid, a lignoceric acid and a cerotic acid.

According to one embodiment therein, the lipid in the nanoparticle is a single type or a mixture of two types or a mixture of two or more lipid types, and wherein the lipid component in the nanoparticle composition is a combination of phospholipid and steroid or preferably a glycolipid or a combination of a phosphatidyl choline and a steroid or more preferably the glycolipid.

According to one embodiment herein, the concentration of hormone or hormone like polypeptide or a thyroid hormone or cytokine or an antibody or an affibody or a combination thereof is in a physiological range of the target cell.

According to one embodiment herein, the nanoparticle has a mean particle size of 50 to 400 nanometer.

According to one embodiment herein, the nanoparticle delivers a gene or a drug, and the gene is selected from a group consisting of a plasmid DNA, a single stranded RNA, a double stranded RNA, a siRNA, a RNA vaccine, an antisense strand of nucleotide and a ribozyme. The drug is selected from a group consisting of a lipophylic drug and a hydrophilic drug.

According to one embodiment herein, a method of synthesizing targeted gene transfer and drug delivery nanoparticle, comprises the steps of preparing a gelatin and chitosan gel. Further a milky colloid solution with the gelatin and chitosan is added with a phosphatidylcholine. The milky colloid solution is subjected to homogenizing in a high speed homogenizer and a high pressure homogenizer for a self assembly of nanoparticles. The last step is transfecting a Chinese Hamster Ovary cells (CHO cells) with the nanoparticles and a lipofectamine 2000 for comparing a transfection efficiency.

According to one embodiment herein, the steps of preparing a gelatin and chitosan gel comprises dissolving 1.76 gram of chitosan in 100 ml of 0.8% of acetic acid and incubating the chitosan solution in a shaker incubator for 16 hours at 37° C. with 120 rpm. The next step is dissolving a 0.4 to 0.6 gram of gelatin in 100 ml of phosphate buffer and incubating the gelatin solution in a shaker incubator for 3 hours at 40° C. with 120 rpm. The 10 ml of dissolved gelatin solution is mixed with the 70 ml of chitosan solution to obtain a solution mixture. The solution mixture is rotated in an incubator shaker for 30 minutes at 37° C. with 140 rpm and obtaining the gelatin chitosan gel.

According to one embodiment herein, the steps of preparing a milky colloid solution comprises dissolving 1.76 gram of chitosan in 100 ml of a 0.8% acetic acid. Further 0.4 to 0.6 gram of gelatin is dissolved in 100 ml of phosphate buffer. The next step is mixing 10 ml of dissolved gelatin with 70 ml of chitosan to obtain a solution mixture. The gelatin and chitosan solution mixture are mixed with a phosphatidyl choline solution. The phosphatidylcholine solution is prepared by dissolving the 0.2 gram of phosphatidylcholine in 10 ml chloroform. After mixing the gelatin and chitosan solution mixture, the milky colloid solution is obtained.

According to one embodiment herein, the step of homogenizing the milky colloid solution for self assembly comprises the steps of pouring a 15 ml of gelatin-chitosan gel into a flask. The gel is stirred on a high speed magnetic stirrer. A 5 ml (200 μl/minute) of milky colloid solution is added to the gel to get a mixture. The mixture is homogenized to obtaining the nanoparticles with a size in the range of 400 nm to 700 nm.

According to one embodiment herein, the step of homogenizing milky colloid solution with a high speed homogenizer comprises the steps of mixing 15 ml of gelatin and chitosan gel with 5 ml of milky colloid in a 50 ml falcon tube to get a mixture. The mixture is subjected to a high speed homogenizer, and obtaining the nanoparticles with a size in the range of 50-400 nm.

According to one embodiment herein, the steps of homogenizing milky colloid solution with a high pressure device comprises mixing 15 ml of gelatin-chitosan gel with 5 ml of milky colloid. The tube is subjected to a high pressure homogenizer, and the nanoparticles with a size in the range of 100-400 nm are obtained.

According to one embodiment herein, the steps of transfecting a Chinese Hamster Ovary cells (CHO) cells, with the nanoparticles comprises culturing the CHO cells at a concentration of $4 \times 10^4$ cells per well into 24 well culture plates containing opti-MEM (1×). 1 μl of pEGFP-N1 plasmid and 2 μl of nanoparticles are diluted separately in a 50 μl of opti-MEM media. The diluted plasmids are incubated at a room temperature for 5 minutes. Equal volumes of the diluted plasmid (50 μl) and the nanoparticles (50 μl) are mixed and incubated at a room temperature for 30 minutes. 100 μl of diluted plasmid and nanoparticles are added into each well of the 24 well culture plate containing CHO cells. The light emitting fluorescent cells are detected 24 hours after transfecting the cells with the nanoparticles. The plasmid transfected cells by the nanoparticles emit a green fluorescent light, and 85% CHO cells are transfected with the nanoparticles facilitated transfection. The concentration of a recombinant protein (sFLT1) is 597 mg/L per cell culture supernatant after the cells are transfected with the plasmid.

According to one embodiment herein, the method of transfecting a Chinese Hamster Ovary (CHO) cells with the lipofectamine 2000 comprises culturing the CHO cells at a concentration of $4 \times 10^4$ cells per well into 24 well culture plates containing opti-MEM (1×). 1 μl of pEGFP-N1 plasmid 2 μl of the lipofectamine 2000 are diluted separately in a 50 μl of opti-MEM media. The diluted plasmids are incubated at a room temperature for 5 minutes. Equal volumes of the diluted plasmid (50 μl) and the lipofectamine 2000 (50 μl) are mixed and incubated at a room temperature for 30 minutes. 100 μl of diluted plasmid and lipofectamine 2000 are added into each well of the 24 well culture plate containing CHO cells. The light emitting fluorescent cells are detected 24 hours after transfecting the cells with the nanoparticles. The plasmid transfected cells by nanoparticles emit a fluorescent light. The rate of cell trasfection is 60-70% when lipofectamine 2000 is used. The concentration of recombinant protein (sFLT1) is 103 mg/L per cell culture supernatant after the cells after the cells are transfected with the lipofectamine 2000.

The various embodiments herein provide a system and a method for the synthesis of the nanoparticle based drug delivery and gene delivery system. The drug or gene delivery nanoparticles are prepared by a combination of chitosan, collagen and phospholipid. The combination of chitosan, collagen and phospholipid provide affinity to gene or drug, controlled release and protection of gene or drug from deterioration until delivery to the target site.

According to one embodiment herein, design of the drug delivery or gene delivery nanoparticles are desired to overcome the pharmaceutical, biopharmaceutical barriers and attach to target cell for gene or drug delivery. The liposomes have potential as a gene delivery vector, however their application are limited to local delivery due to low stability and rapid degradation in the body. The chitosans are cationic polymers and are used to deliver DNA both in vitro and in vivo. The chitosans exhibit low cytotoxicity. The chitosans have problems such as relative inefficiency and low specificity.

According to one embodiment herein, the combination of chitosan, collagen and phospholipid for the synthesis of drug or gene delivery nanoparticles provide the affinity to gene or drug targeting, controlled release and protection of the gene or drug from deteriorating prior target release. The improved nanoparticle composition for targeted gene transfer and drug delivery with a complex of a cell targeting ligand consists of protein, chitosan and lipid or a derivative thereof. The protein in nanoparticles is collagen (type I or II or III or IV or V or VI or VI or VII or VII) or gelatin or a derivative thereof or elastin or hormone (like polypeptide or thyroid hormone or cytokine or antibody or affibody or a combination thereof. The lipid in nanoparticles is phospholipid or steroid or glycerol ormonoglyceride or diglyceride or triglyceride or fat soluble vitamin or saturated or unsaturated free fatty acid or glycolipid or a derivative thereof or a combination thereof.

According to one embodiment herein, the chitosan is obtained from the deacetylation of chitin. The chitin is naturally occurring biocompatible polysaccharide. Chemically the chitosan comprises of a 2-acetamido-2-deoxy-β-D-glucan (1-4) linked to 2-amino-2deoxy-β-D-glucan. The deacetylated group possesses three reactive functional groups such as an amine group, a primary hydroxyl group and a secondary hydroxyl group. The amine groups have a pKa value of 6.5, making chitosan a pH responsive polymer. At a pH of 7.4 the amine backbone of chitosan is neutral, while at a pH of 5.5 more than 90% of the amine groups are protonated making chitosan soluble in organic acids. The role of chitosan for nucleic acid delivery is the interaction with the positive charge of amine groups, which bind to negatively charged molecules such as nucleic acids, and form positively charged nano-sized complexes. The nanoparticles from chitosan are prepared by covalent crosslinking with glutaraldehyde. Chitosan has a positive charge in acidic condition due to the amino groups and generate electrostatic complexes with polyanions to produce nanoparticles. The nanoparticles thus formed are non-toxic and are used for adhering to the mucosal surface and transiently opening the tight junctions between epithelial cells and for intravenous drug delivery systems to brain via blood brain barrier.

The chitosan nanoparticles are suitable for drug delivery in acidic pH conditions but transferring of nanoparticles to physiological pH increased in nanoparticle size and cluster. For the synthesis of drug and gene delivering nanoparticles, chitosan with molecular weights ranging from 1 KDa to 500 kDa or 10 KDa to 90 kDa and with a degree of deacetylation at least 70% is used in combination with other components. The concentration of chitosan in nanoparticles is from 0.01 to 0.05 mmol, preferably from 0.05 to 0.03 mmol and more preferably from 0.07 to 0.2 mmol.

According to one embodiment herein, the nanoparticle composition for gene or drug delivery consists of lipid. The lipid is phospholipid or steroid or glycerol or monoglyceride or diglyceride or triglyceride or fat soluble vitamin or saturated or unsaturated fatty acid or glycolipid or a derivative thereof or a combination of thereof.

The phospholipid(s) includes: 1) Phosphatidylcholines such as di-stearoylphosphatidylcholine, di-linoleoylphosphatidylcholine, di-oleoylphosphatidylcholine, myristoylpalmitoylphosphatidylcholine, myristoylstearoylphosphatidylcholine, di-lauroylphosphatidylcholine, di-myristoylphosphatidylcholine, di-palmitoylphosphatidylcholine, and palmitoylstearoylphosphatidylcholine; 2) Phosphatidylglycerols include di-lauroylphosphatidylglycerol, di-myristoylphosphatidylglycerol, di-palmitoylphosphatidylglycerol, di-stearoylphosphatidylglycerol, di-oleoylphosphatidylglycerol, di-linoleoylphosphatidylglycerol, myristoylpalmitoylphosphatidylglycerol, myristoylstearoylphosphatidylglycerol, and palmitoylstearoylphosphatidylglycerol; 3) Phosphatidylethanolamines include di-palmitoylphosphatidylethanolamine, di-myristoylphosphatidylethanolamine, myristoylpalmitoylphosphatidylethanolamine, di-stearoylphosphatidylethanolamine, di-oleoylphosphatidylethanoamine, di-lauroylphosphatidylethanolamine, di-linoleoylphosphatidylethanolamine, myristoylstearoylphosphatidylethanolamine, and palmitoylstearoylphosphatidylethanolamine; 4.) Phosphatidic acid; 5) Phosphatidylserine; 6) Sphingomyelin; 7) Phosphatidylinositol; 8) Cardiolipin; and 9) Lecithin from soybean egg yolk.

A steroid is a type of organic compound that contains a characteristic arrangement of four cycloalkanes rings that are joined to each other. The steroids include corticosteroids (glucocorticoids and mineralocorticoids), sex steroids (androgens, estrogens and progesterone), cholesterol, bile acids, sterol and a derivative thereof. The three cyclohexane rings form the skeleton of phenanthrene and has a ring of cyclopentane structure. Hence they are together called cyclopentaphenanthrene. The steroid fraction is present in nanoparticle in a concentration such that the steroid acts as a hormone in the physiological range of targeted cell adhesion.

The glycolipid includes glycerol glycolipids such as diglyco syldiglyceride, di-galactosyldiglyceride, galactosyldiglyceride, and glycosyldiglyceride; glycosphingolipids such as galactosylcerebroside and; stearylglucoside; and ganglioside esterified stearylglycoside.

The unsaturated free fatty are myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

The saturated free fatty acids caprylic acid, capric acid, lauric acid, myristic acid, palmitic acid, stearic acid, arachidic acid, behenic acid, lignoceric acid and cerotic acid.

These constituent lipids of the nanoparticle may be used alone, or two or more kinds of them may be used in combination. The lipid constituent of the nanoparticle is a combination of phospholipid(s) and steroid or preferably glycolipid or a combination of phosphatidylcholine and steroid or more preferably glycolipid.

The functions of phospholipid(s) are the electrostatic attraction between the charged groups of the nanoparticles and regulating the gene or drug delivery; solubility of lipid component of nanoparticles and facilitating the transfection of nanoparticle to the targeted cell. The phospholipid (s) and steroid and glycolipid are used in a combination and the content of the lipid constituent of the nanoparticle is not specifically limited and it is from 0.01 mmol to 200 mmol, preferably from 0.1 to 50 mmol, and more preferably from 1 to 20 mmol.

According to one embodiment herein, the protein component in the gene or drug delivery nanoparticle comprises the various types of collagen (type I or II or III or IV or V or VI or VII or VIII) or gelatin or a derivative thereof or elastin or hormone or hormone like polypeptide or thyroid hormone or cytokine or antibody or affibody or combination of them and steroid and glycolipid regulate of targeting cellular function. Also hormone or hormone like polypeptide or thyroid hormone or cytokine or antibody or affibody or steroid or fat-soluble vitamin or combination of them. The protein component of the nanoparticle regulates the cell function before and/or after gene or drug delivery from nanoparticle into the targeted cell.

The proteins that consist of collagen, type I or II or III or IV or V or VI or VII or VIII or gelatin or a derivative thereof, that contain the RGD (Arg-Gly-Asp) tripeptide motif system or the triple-helical pitch of collagen or elastin or hormone or hormone like polypeptide or thyroid hormone or cytokine or antibody or affibody or combination of them are used in the content of the constituent protein of the nanoparticle synthesis is not specifically limited and it is from 0.005 mmol to 1 mmol, preferably from 0.05 to 0.5 mmol, and more preferably from 0.01 to 0.1 mmol.

The helical pitch of collagen changes across the domains and types of collagen or gelatin or a derivative thereof or a combination of them, which contain the RGD (Arg-Gly-Asp) tripeptide motif system, recognized the targeted cell.

The concentration or the protein that act as hormone or constituent hormone or hormone like polypeptide or thyroid hormone or cytokine or antibody or affibody or combination of them in the nanoparticle, is in the physiologic range of targeted cell action.

According to one embodiment herein, the nanoparticle system for gene delivery or drug delivery requires 1) A motif system for specific cell adhesion or cell signaling or combination of them: a) Collagen, type I or II or III or IV or V or VI or VII or VIII or gelatin or a derivative thereof, that contain the RGD (Arg-Gly-Asp) tripeptide or the triple-helical pitch of collagen or elastin or combination of them act as the system of nanoparticle for specific cell adhesion or cell signaling or combination of them; b) The steroid hormone or hormone like polypeptide or thyroid hormone or cytokine or antibody or affibody or combination of them act as the motif system of nanoparticle for specific cell adhesion or cell signaling or combination of them. 2) Chitosan, when protonated at an acidic pH exhibits the following properties and functions: a) Chitosan, is cationic polymer and facilitate nanoparticle attach to cell and potential as a gene or drug delivery vector; b) Chitosan, undergoes ionic gelation, due to the electrostatic interaction between the phospholipid(s), collagen and gene or drug with charged ions, c) Chitosan, has the ability to open intercellular tight junctions and facilitating its transport into the target cells. 3) The lipid is a phospholipid(s) or sterol or steroid or glycerol ormonoglyceride or diglyceride or triglyceride or fat-soluble vitamin or saturated or unsaturated free fatty acid or glycolipid or a derivative thereof or combination of them act as: a) Affect the cell membrane flexibility for attachment and in turn the nanoparticle release into cell, b) Steroid hormone cause modulating fluidity of the nanoparticle and regulation of targeted cell function and c) Fat-soluble vitamin or derivatives thereof act hormone-like functions as regulation of cell function of targeted cell.

According to one embodiment herein, the electrostatic attraction between charged group of the proteins or a derivative thereof and the phosphate groups of the phospholipid or a derivative thereof and amino groups of chitosan or a derivative thereof in nanoparticle cause electrostatic regulatory for gene and drug delivery in physiological condition.

The nanoparticle formation is because of the increase the electrostatic attraction between chitosan and phospholipid via the amino and phosphate groups. The other bonding or molecular interactions are hydrogen bond between the —OH groups and the NH groups of collagen or gelatin. The lipid component consists of steroid or glycolipid or fat soluble vitamin. The nanoparticles formation in the composition of the "collagen and/or gelatin, phospholipid and chitosan" cause electrostatic attraction and results in the regulated gene or drug binding capacity of the nanoparticles. The chitosan, phospholipid and collagen and/or gelatin and gene or drug undergoes iconic gelation due to the electrostatic interaction between the oppositely charged ions. The hydrophobic lipid tails affect the cell membrane flexibility for attachment and release of the drug or gene into the cell.

According to one embodiment herein, the drug and the gene delivery nanoparticle formed and shaped by self assembling or high speed stirring method or high pressure method, ethanol injection method or ultrasonification method and the diameter is modulated by an extrusion or homogenization or French press method. The mean particle size of the nanoparticles is between 50 and 400 nanomaters.

FIG. 1 is a flowchart illustrating the process of synthesizing non-viral drug and gene delivery nanoparticle, according to an embodiment herein. The first step in the synthesis of non-viral of non-viral gene or drug delivery nanoparticles is preparing a gelatin and chitosan gel (101). The next step is preparing a milky colloid solution with chitosan and gelatin gel with phosphatidylcholine (102). The milky colloid solution is homogenized for the self assembly of nanoparticles (103). The milky colloid solution is homogenized in high speed homogenizer and high pressure homogenizer. The Chinese Hamster Ovary Cells (CHO cells) are transfected with nanoparticles and lipofectamine to compare the transfection efficiency (104).

Figure 2:
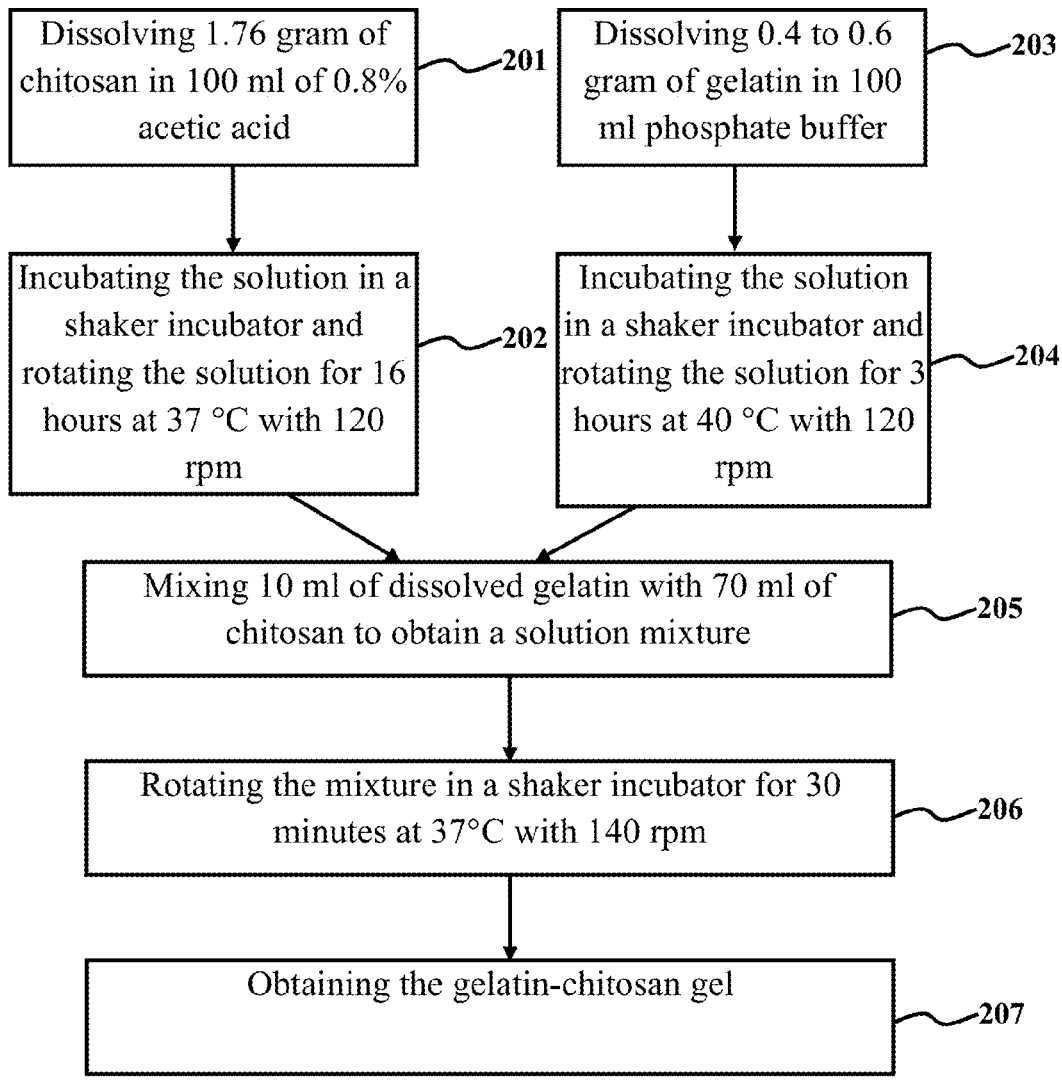
FIG. 2 is a flowchart illustrating preparation of gelatin-chitosan gel, according to an embodiment herein.

FIG. 2 is a flowchart illustrating preparation of gelatin-chitosan gel, according to an embodiment herein. The first step is dissolving 1.76 gram of chitosan in 100 ml of 0.8% of acetic acid (201). The chitosan solution is incubated in a shaker incubator and the solution is rotated for 16 hours at 37° C. with 120 rpm (202). Dissolving a 0.4 to 0.6 gram of gelatin in 100 ml of phosphate buffer (203). The gelatin solution is incubated in a shaker incubator and the solution is rotated for 3 hours at 40° C. with 120 rpm (204). The next step is mixing 10 ml of dissolved gelatin with 70 ml of chitosan solution to obtain a solution mixture (205). The solution mixture is rotated in a shaker incubator for 30 minutes at 37° C. with 140 rpm (206). After incubation the gelatin-chitosan gel is obtained (207).

Figure 3:
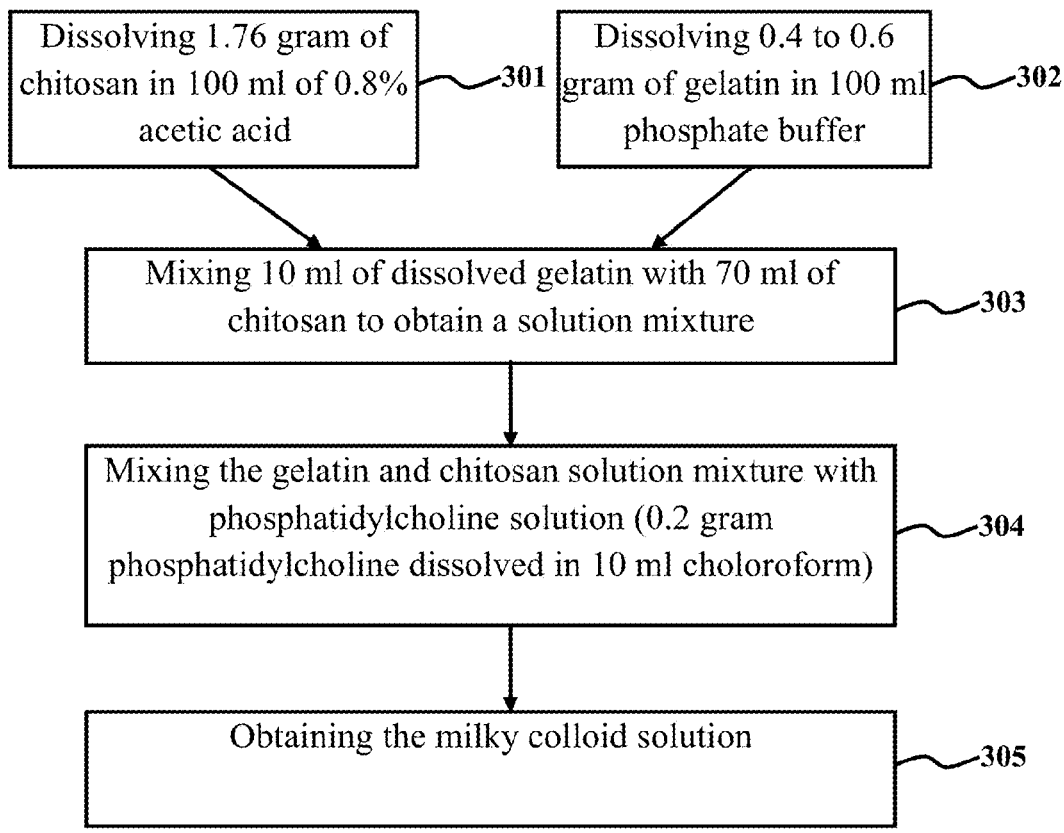
FIG. 3 is a flowchart illustrating preparation of a milky colloid solution, according to an embodiment herein.

FIG. 3 is a flowchart illustrating preparation of a milky colloid solution, according to an embodiment herein. The first step is dissolving 1.76 gram of chitosan in 100 ml of 0.8% acetic acid (301). Second step is dissolving 0.4 to 0.6 gram of gelatin in 100 ml of phosphate buffer (302). The next step is mixing 10 ml of dissolving gelatin with 70 ml of chitosan to obtain a solution mixture (303). Further mixing the gelatin and chitosan solution mixture with phosphatidylcholine solution (0.2 gram of phosphatidylcholine dissolved in 10 ml chloroform) (304). The last step is obtaining the milky colloid solution (305).

Figure 4:
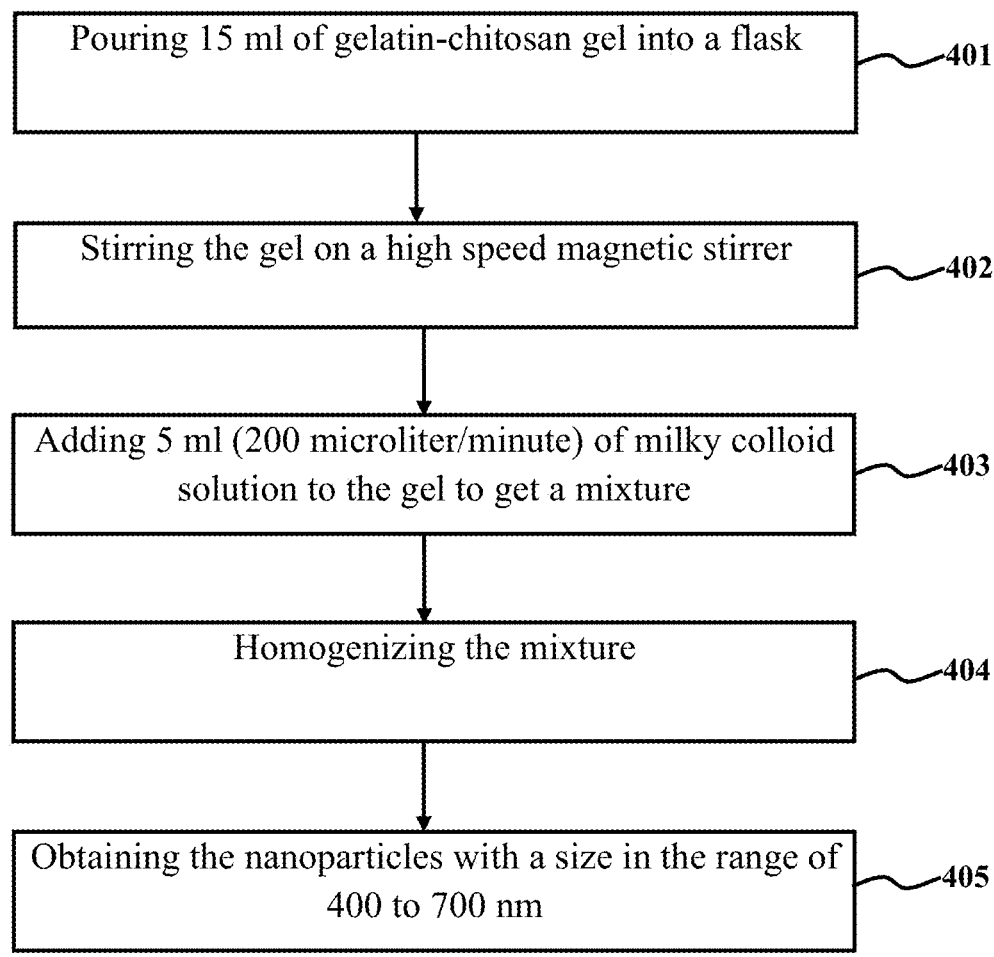
FIG. 4 is a flowchart illustrating preparation of self assembling nanoparticles, according to an embodiment herein.

FIG. 4 is a flowchart illustrating preparation of self assembling nanoparticles, according to an embodiment herein. The first step is pouring 15 ml of gelatin-chitosan gel into a flask (401). Stirring the gel on a high speed magnetic stirrer (402). Adding 5 ml (200 microliter/minute) of milky colloid solution to the gel to get a mixture (403). Homogenizing the mixture (404). Obtaining the nanoparticles with a size in the range of 400 to 700 nm (405).

Figure 5:
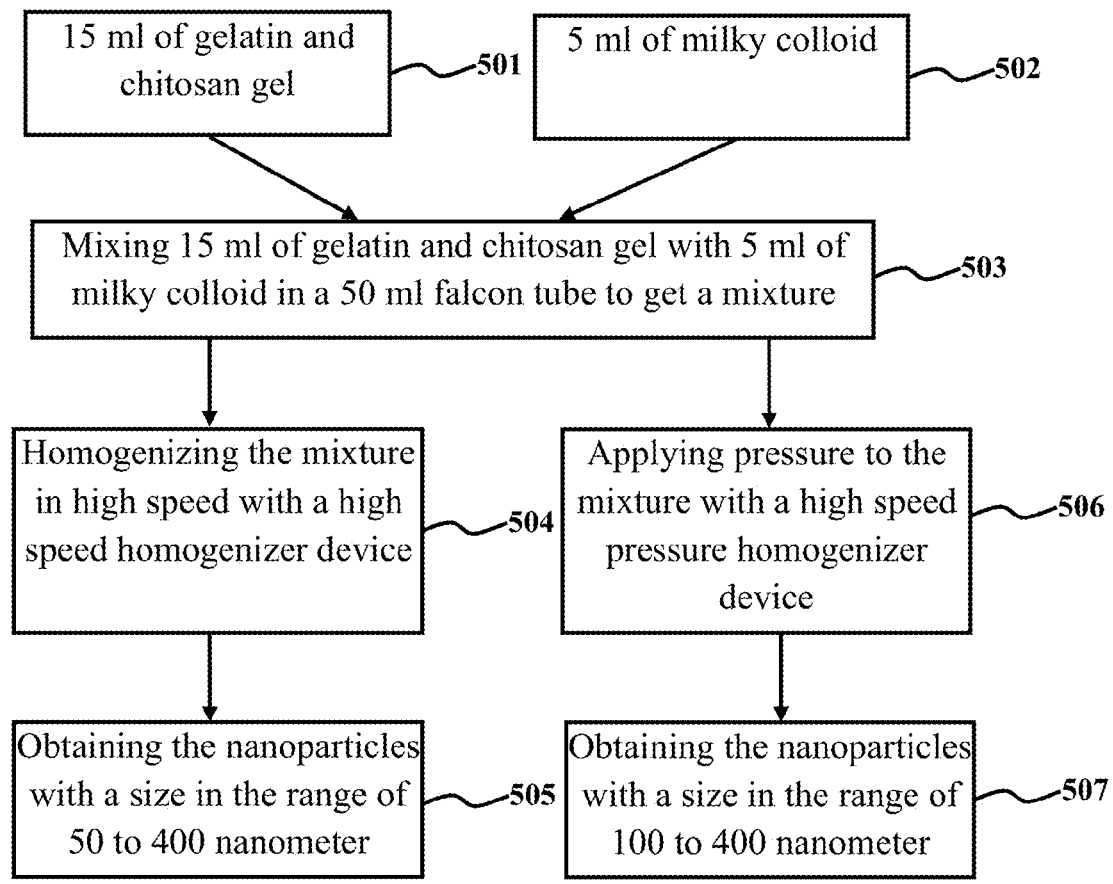
FIG. 5 is a flowchart illustrating a nanoparticle preparation with high speed and high pressure device, according to an embodiment herein.

FIG. 5 is a flowchart illustrating nanoparticle preparation with high speed and high pressure device, according to an embodiment herein. The first step is 15 ml of gelatin and chitosan gel is taken (501) and 5 ml of milky colloid solution is taken (502). The second step is mixing 15 ml of gelatin and chitosan gel with 5 ml of milky colloid in a 50 ml falcon tube to get a mixture (503). For preparing the nanoparticles with high speed homogenizer the mixture is homogenized in high speed with a high speed homogenizing device (504). The nanoparticles with a size in the range of 50 to 400 nm are obtained (505). For preparing the nanoparticles with high pressure device the pressure is applied to the mixture with a high speed pressure homogenizer device (506). The nanoparticles with a size in the range of 100 to 400 nm are obtained (507).

EXAMPLE 1

Preparation of Gelatin-chitosan Gel and Milky Colloid Solution with Gelatin-chitosan Gel and Phosphatidylcholines 1.76 gram of chitosan with a molecular mass of 90 kDa and a degree of deacetylation of 80% was dissolved in 100 ml of 0.8% acetic acid. The solution was rotated in a shaker incubator for 16 hrs at 37° C. with 120 rpm. Thereafter, it was centrifuge for 15 minutes at 4000 rpm. The gel in supernatant was taken off. Then 0.4 to 0.6 gram of gelatin (type A) in 100 ml of phosphate buffer was dissolved in a shaker incubator for 3 hrs at 40° C. with 120 rpm. 10 ml of dissolved gelatin was mixed with 70 ml of chitosan and kept in shaker incubator for 30 minutes at 37° C. with 140 rpm. In a glass round bottle flask, 0.2 gram phosphatidycholine (lecithin) was dissolved with 10 ml of chloroform and after removing the chloroform by rotary vacuum evaporator, lecithin was precipitated in inner wall of flask and dispersed stably in the solution of gelatin-chitosan to obtain a milky colloid solution

EXAMPLE 2

Preparation of Nanoparticles by Self Assembly 15 ml of gelatin-chitosan gel was poured into flask and kept on high speed magnetic stirrer. Slowly, 5 ml (200 microliter/minutes) of milky colloid solution was added to it and homogenized. The nanoparticles were formed by self-assembly. The size of nanoparticles is in a range of 400-700 nanometers.

EXAMPLE 3

Nanoparticle Preparation with High Speed Device

In 50 ml falcon-tube, 15 ml of gelatin-chitosan gel was mixed with 5 ml of milky colloid and the tube was kept in a high speed homogenizer. The nanoparticles produced have the size in a range of 50-400 nanometers.

EXAMPLE 4

Nanoparticle Preparation with High Pressure Device

In 50 ml falcon-tube, 15 ml of gelatin-chitosan gel mixed with 5 ml of milky colloid and the tube kept in high pressure homogenizer. Nanoparticles produced and the sizes are between 100-400 nanometers. The nanoparticles in three examples analyzed by AFM and the shape, diameter and stability compare with lipofectamin 2000.

Figure 6:
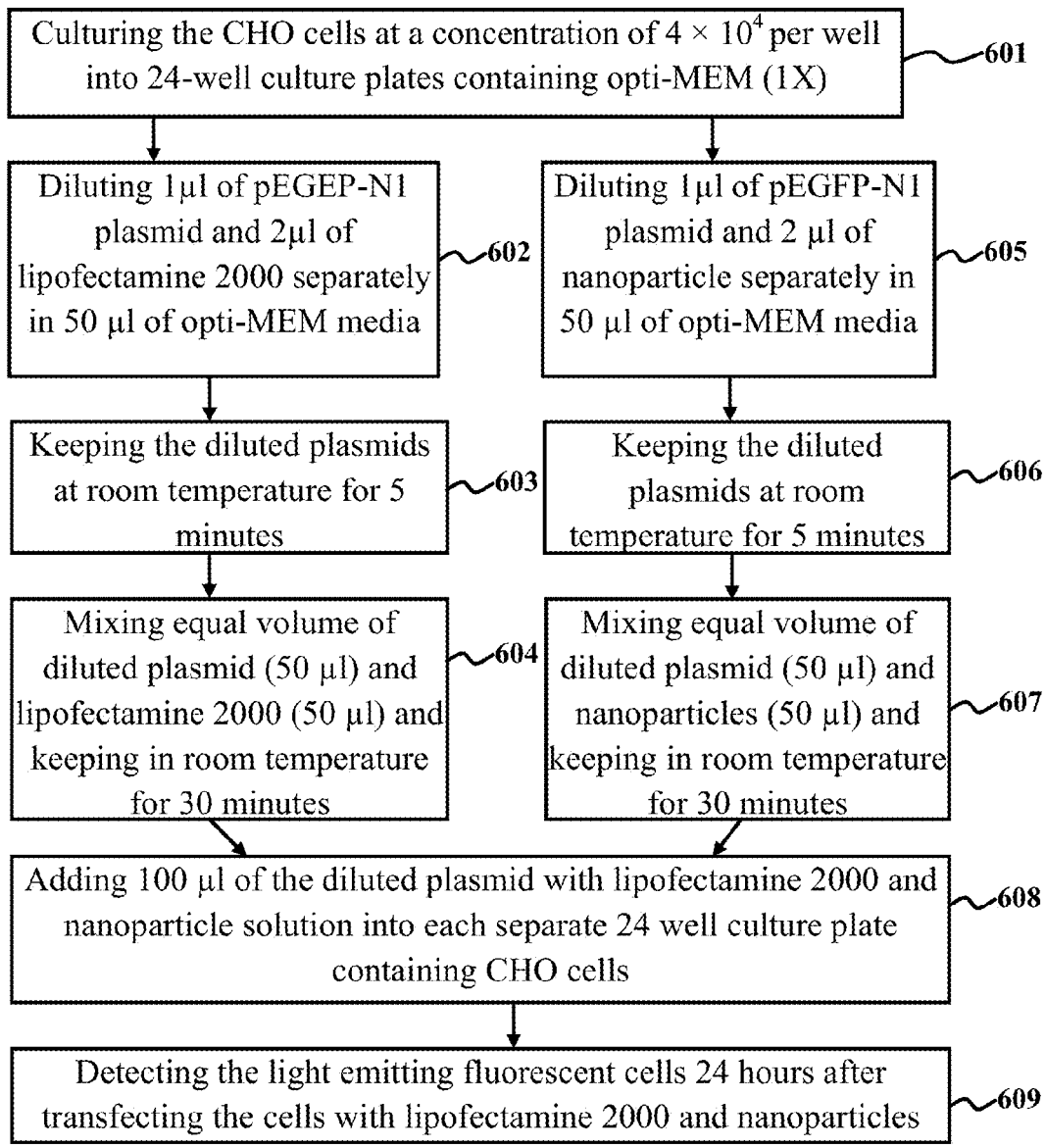
FIG. 6 is a flow chart illustrating a process of comparison between the CHO cells transfected with nanoparticle and lipofectamine, according to one embodiment herein.

FIG. 6 is a flow chart illustrating the comparison between the CHO cells transfected with nanoparticle and lipofectamine, according to one embodiment herein. The first step is culturing the CHO cells at a concentration of $4 \times 10^4$ per well into 24-well culture plates containing opti-MEM (1×) (601). For transfection of the CHO cells with lipofectamin, 1 µl of pEGEP-N1 plasmid and 2 µl of lipofectaine 2000 are diluted separately in 50 µl of opti-MEM media (602). The diluted plasmids are kept at room temperature for minutes (603). Equal volume of diluted plasmid (50 µl) and lipofectamine 2000 (50 µl) are mixed and kept in a room temperature for 30 minutes (604). For transfection of the CHO cells with nanoparticles, 1 µl of pEGFP-N1 plasmid and 2 µl of nanoparticles are separately diluted in 50 µl of opti-MEM media (605). The diluted plasmids are kept at room temperature for 5 minutes (606). Equal volume of diluted plasmid (50 µl) and nanoparticles (50 µl) are mixed and kept in room temperature for 30 minutes (607). Adding 100 µl each of diluted plasmid with lipofectamine 2000 solution and diluted nanoparticle with nanoparticle solution into each separate 24 well culture plate containing CHO cells (608). Detecting the light emitting fluorescent cells 24 hours after transfecting the cells with lipofectamine 2000 and nanoparticles (609).

EXAMPLE 5

Comparison of CHO Transfection with Nanoparticles and Lipofectsmine

For the gene expression and Protein production in transfected CHO cell lines by lipofectamine 2000 &nanoparticles: The in-vitro secretion of protein and fluorescent emitted light production in transfected CHO cells with pEGFP-N1 plasmid that contain sFLT1 (soluble vascular endothelial growth factor) gene fragment, detected by the level of protein secretion. CHO cells culture at a concentration of $4 \times 10^4$ per well into 24-well culture plates containing Opti-MEM under Standard protocol transfection: 1 µl of pEGFP-N1 plasmid and 2 µl of lipofectamine 2000 was diluted separately in 50 µl of Opti-MEM media, kept at room temperature for 5 minutes and equal volume of diluted plasmid (50 µl) and lipofectamine 2000 (50 µl) were mixed together and remained at room temperature for 30 minutes and 100 µl of this solution added into each well into 24-well culture plates and similar steps used for nanoparticle. After 24 hours, the culture plates were investigated under inverted Florescent-microscopy. The transfected cells with pEGFP-N1 plasmid emit a green florescent light. The rate of cell transfection reached to 60-70% when lipofectamine 2000 (standard liposome) used. The obtained concentration of recombinant protein (sFLT1) with this liposome was 103 mg/L in cell culture supernatant and the rate of cell transfection with nanoparticles more than 85% number of cells and concentration of recombinant protein (sFLT1) by nanoparticles was 587 mg/L per cell culture supernatant.

Figure 7A:
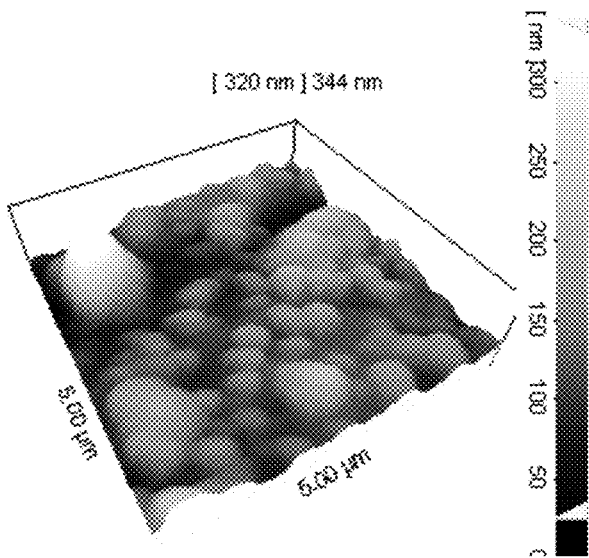
FIG. 7A-7B is a 3D adapted AFM image illustrating the standard lipofectamin 2000, according to one embodiment herein.
Figure 7B:
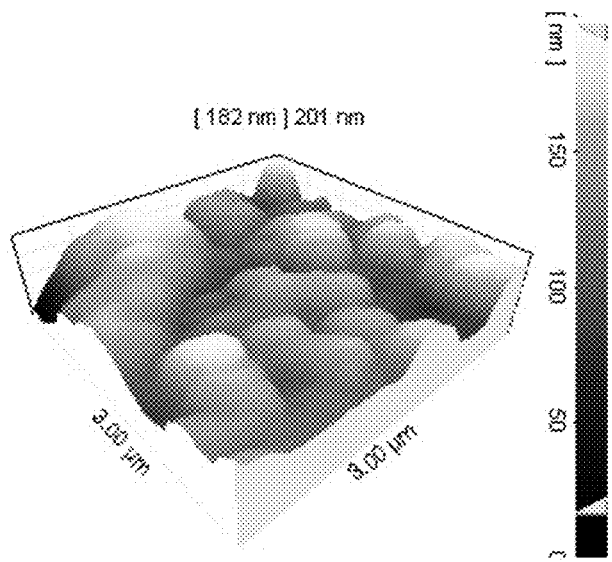

FIG. 7A-7B is a 3D adapted AFM image illustrating the standard lipofectamin 2000, according to one embodiment herein. The size of lipofectamine 2000 nanoparticle observation by the AFM shows heterogeneous particles in different sizes, nano-sized particles having a size of 500 nm.

Figure 8A:
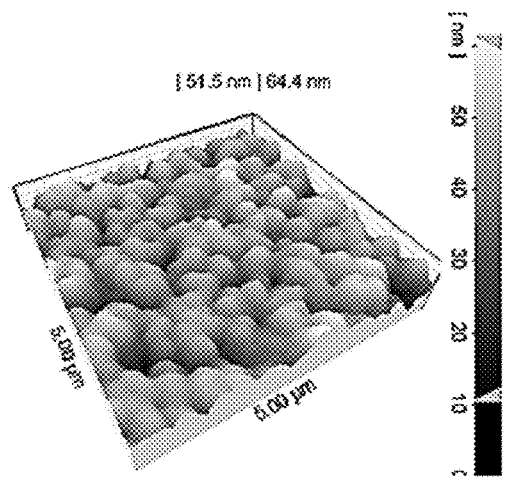
FIG. 8A-8C is a 3D adapted AFM image of chitosan-collagen-phosphatidylcholine, according to one embodiment herein.
Figure 8B:
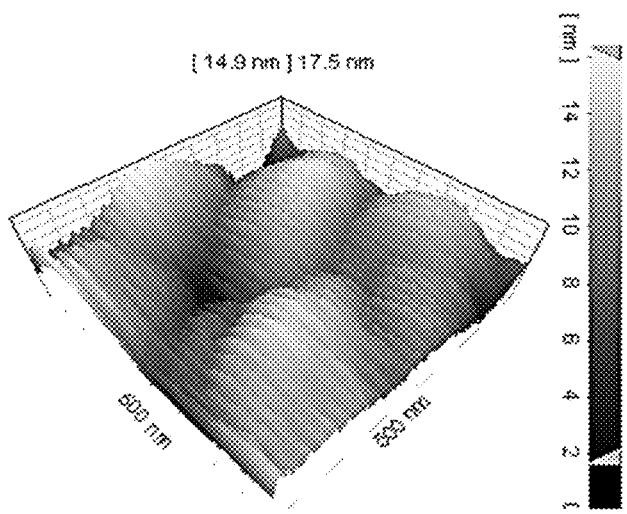
Figure 8C:
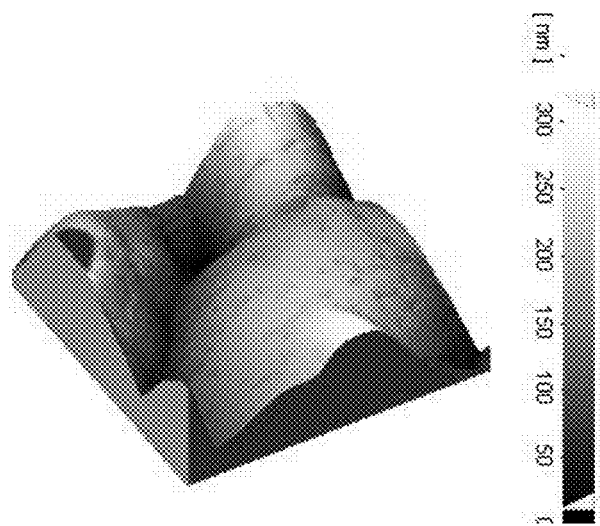
Figure 9A:
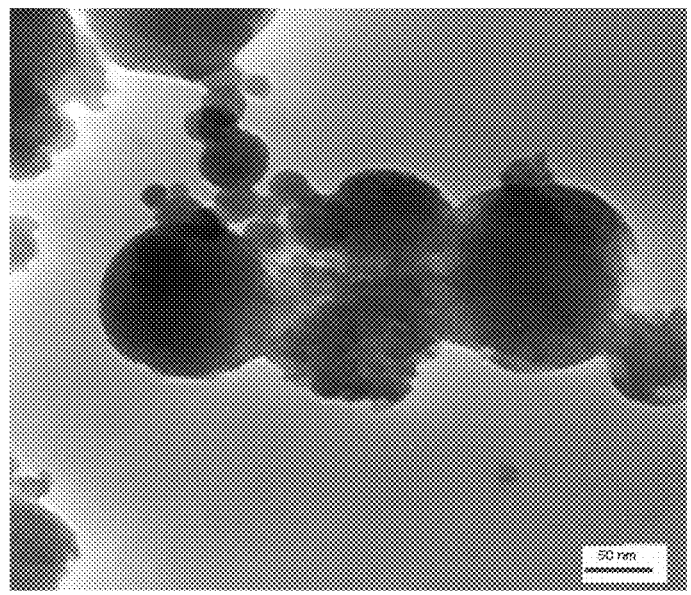
FIG. 9A-9F is a transmission electron microscope image of chitosan-collagen-phosphatidylcholine, according to one embodiment herein.
Figure 9B:
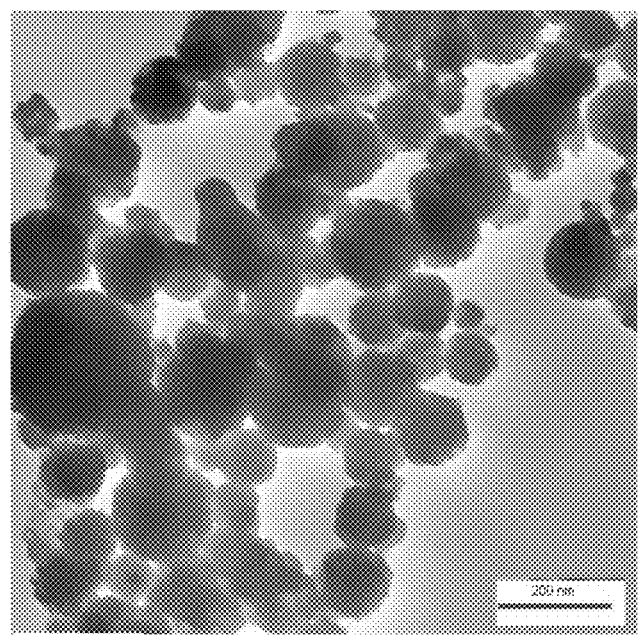
Figure 9C:
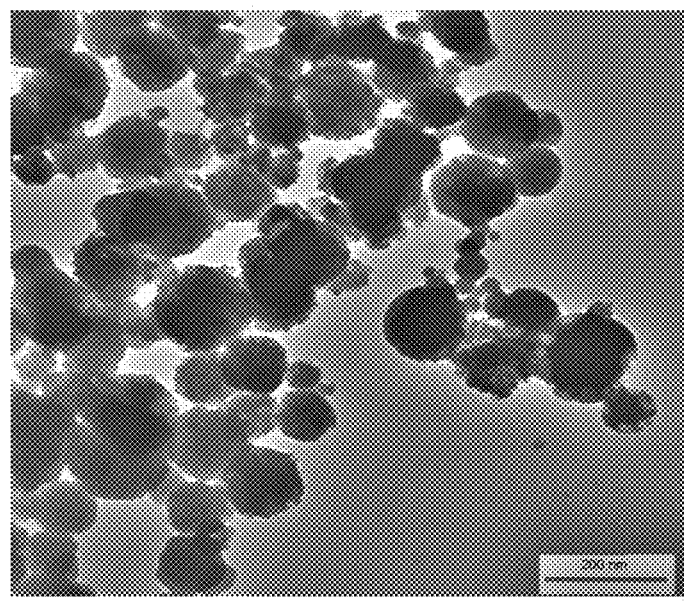
Figure 9D:
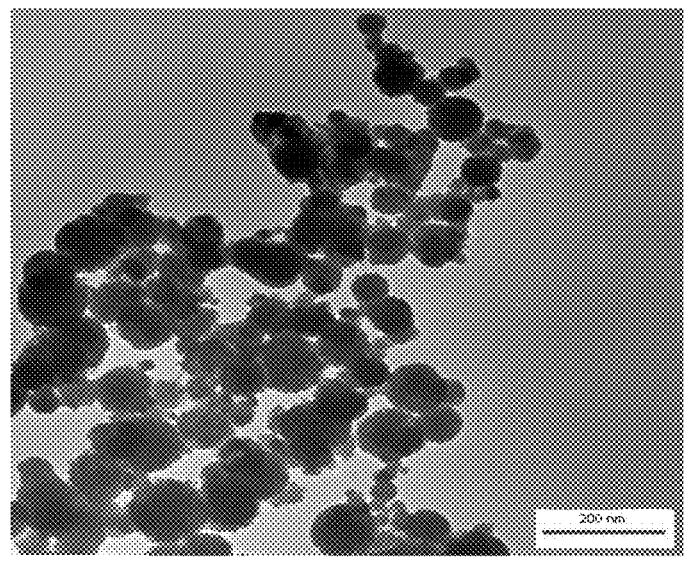
Figure 9E:
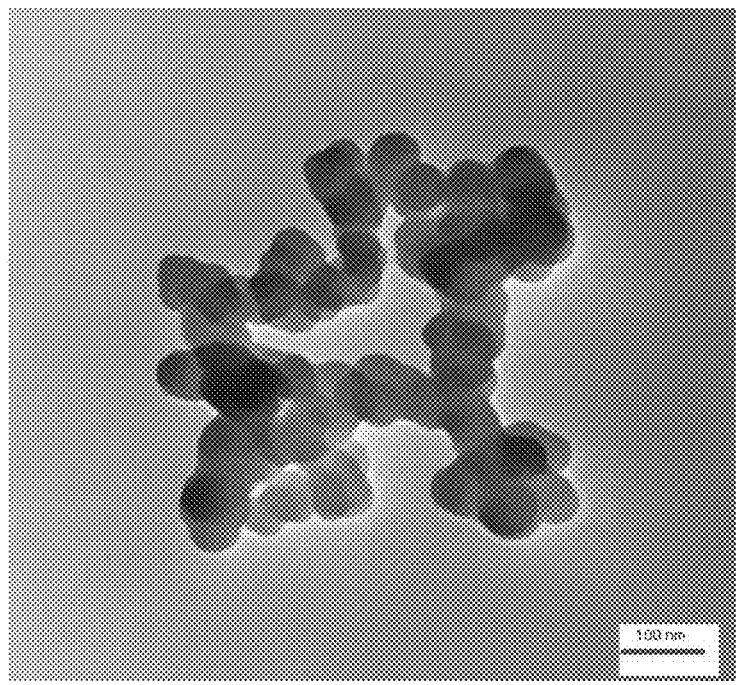
Figure 9F:
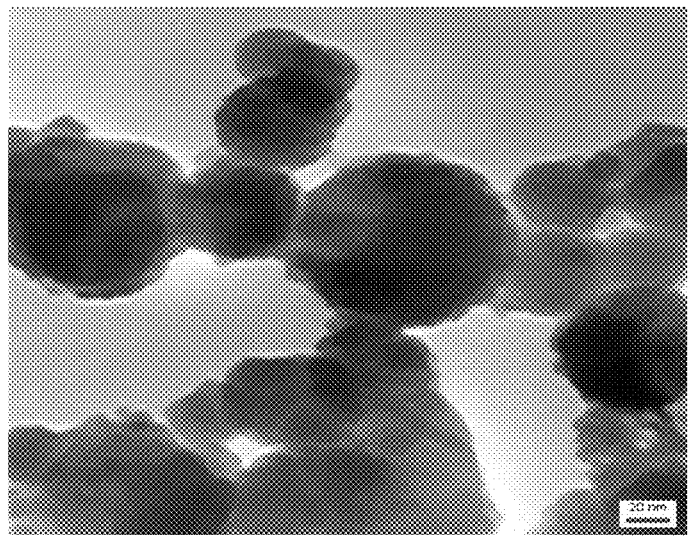

FIG. 8A-8C is a 3D adapted AFM image of chitosan-collagen-phosphatidylcholine, according to one embodiment herein. The size of chitosan-gelatin-phosphatidylcholine nanoparticle observed by the 3d-Adapted AFM images illustrates the homogenous particles in sizes of about 200-300 nm.

FIG. 9A-9F is a transmission electron microscope image of chitosan-collagen-phosphatidylcholine, according to one embodiment herein. The size of chitosan-gelatin-phosphatidylcholine nanoparticle analyzed by Transmission Electron Microscopic (TEM) image shows round shape semi homogenous particles with a size in the range of 100-300 nm.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A nanoparticle composition for targeted nucleic acid transfer and drug delivery to a cell comprising:
   a cell targeting ligand comprising a complex of a protein, a chitosan, and a lipid;
   wherein the chitosan is positively charged, and wherein the lipid has a negative charge, and wherein the protein, the chitosan and the lipid have an electrostatic attraction,
   and wherein the nucleic acid is selected from the group consisting of a plasmid DNA, a single stranded RNA, a double stranded RNA, a siRNA, a RNA vaccine, an antisense nucleic acid and a ribozyme, and wherein the drug is selected from the group consisting of a lipophylic drug and a hydrophilic drug.

2. The nanoparticle composition according to claim 1, wherein the protein is selected from a group consisting of a collagen, a gelatin, an elastin, a derivative of the elastin, tripeptide motif system having Xaa position, a hormone, a cytokine, an antibody, an affibody, or a combination thereof, and wherein the collagen is a collagen of type I or type II or type III or type IV or type V or type VI or type VII or type VIII, and wherein the hormone is a thyroid hormone or a polypeptide hormone, and wherein the tripeptide motif system is Arg-Gly-Asp (RGD)tripeptide motif system, and wherein the Arg-Gly-Asp (RGD)tripeptide motif system recognizes the target cell, and wherein the protein performs cell adhesion or cell signaling or both, and wherein the protein has a concentration of 0.005 mmol to 1 mol, and wherein the protein has a concentration preferably in a range of 0.05 to 0 5 mmol, and wherein the protein has a concentration more preferably in a range of 0.01 to 0.1 mmol.

3. The nanoparticle composition according to claim 1, wherein the lipid is selected from a group consisting of a phospholipid, sterols, a steroid, a glycerol, a monoglyceride, a diglyceride, a triglyceride, a fat soluble vitamin, a saturated fatty acid, an unsaturated fatty acid, and a glycolipid or a combination thereof, and wherein the phospholipid is neutral or anionic, and wherein the phospholipid has the hydrophobic lipid tails, and wherein the concentration of the lipid is in a range of 0.01 mmol to 200 mmol, preferably in a range of 0.1 to 50 mmol and more preferably in a range of 1 to 2 mmol.

4. The nanoparticle composition according to claim 3, wherein the phospholipid is selected from a group consisting of a phosphatidyl choline, a phosphatidyl glycerol, a phosphatidylethanolamine, a phisphatidic acid, a phosphatidyl serine, a sphingomyelin, a phosphatidyl inositol, a cardiolipid and a lecithin, and wherein the phosphatidyl choline is selected from a group consisting of a di-stearoylphosphatidyl choline, a di-inoleoylphosphatidyl choline, a dioleoylphosphatidyl choline, a myristoylpalmitoylphosphatidyl choline, a myristoylstearoylphosphatidyl choline, a dilauroylphosphatidyl choline, a dimyrostoylphosphatidyl choline, a dipalmitoylphosphatidyl choline and a palmitoylstearoylphosphatidyl choline, and wherein the phosphatidyl glycerol is selected from a group consisting of a dilauroylphosphatidyl glycerol, a dimyristoylphosphatidyl glycerol, a dipalmitoylphosphatidyl glycerol, a distearoylphosphatidyl glycerol, a dioleoylphosphatidyl glycerol, a dilinoleoylphosphatidyl glycerol, a myristoylpalmitoyl, a phosphatidyl glycerol, a myristoylstearoylphosphatidyl glycerol and a palmotoylstearoylphosphatidyl glycerol, and wherein the phosphatidyl ethanolamine is selected from a group consisting of a dipalmitoylphosphatidyl ethanolamine, a dimyristoylphosphatidyl ethanolamine, a myristolpalmitoylphosphatidyl ethanolamine, a distearoylphosphatidyl ethanolamine, a dioleoylphosphatidyl ethanolamine, a dilauroylphosphatidyl ethanolamine, a dilinoleoylphosphatidyl ethanolamine, a myristoylsteroylphosphatidyl ethanolamine and a palmitoylstearoylphosphatidyl ethanolamine, and wherein the phospholipid induces an electrostatic attraction between charged groups of the nanoparticles to regulate a gene or a drug delivery, to regulate a solubility of a lipid component of nanoparticles and to transfect the nanoparticles to the target cell.

5. The nanoparticle composition according to claim 3, wherein the steroid is selected from a group consisting of a corticosteroid, a sex steroid, a cholesterol, a bile acid, and a sterol, and wherein the steroid modulates the fluidity of the nanoparticle and regulation of the target cell function, and wherein the corticosteroid is selected from a group consisting of a glucocorticoid and a mineralocorticoid, and wherein the sex steroid is selected from a group consisting of an androgen, an estrogen, and a progesterone.

6. The nanoparticle composition according to claim 3, wherein the glycolipid is selected from a group consisting of a glycerol glycolipid, a glycosphingolipid, a stearyl glycoside and a ganglioside esterified stearyl glycoside, and wherein the glycerol glycolipid is selected from a group consisting of a diglycosyl di glyceride, a digalactosyl di glyceride, a galactosyl di glyceride and a glycosyldi glyceride, and wherein the glycosphingolipid is selected from a group consisting of a galactocerebroside, a stearylglucoside, and a ganglioside esterified stearylglycoside and wherein the glycolipid causes stability of nanoparticles and attachment to a target cell membrane.

7. The nanoparticle composition according to claim 3, wherein the unsaturated fatty acid is selected from a group consisting of a myristoleic acid, a palmitoleic acid, a sapienic acid, an oleic acid, an elaidic acid, a vaccenic acid, a linoleic acid, a linoelaidic acid, α-linolenic acid, an arachidonic acid, an eicosapentaenoic acid, an erucic acid and a docosahexanoic acid.

8. The nanoparticle composition according to claim 3, wherein the saturated fatty acid is selected from a group consisting of a caprylic acid, a capric acid, a lauric acid, a myristic acid, a palmitic acid, a stearic acid, an arachidic acid, a behenic acid, a lignoceric acid and a cerotic acid.

9. The nanoparticle composition according to claim 3, wherein the lipid in the nanoparticle is a single type or a mixture of two types or a mixture of two or more lipid types, and wherein the lipid constituent in the nanoparticle composition is a combination of phospholipid and a steroid, or more preferably the glycolipid or a combination of a phosphatidyl choline and a steroid.

10. The nanoparticle according to claim 1, wherein the nanoparticles of the composition have a mean particle size of 50 to 400 nanometer.

* * * * *